United States Patent
Noecker et al.

(10) Patent No.: US 6,454,742 B1
(45) Date of Patent: Sep. 24, 2002

(54) VALVE CUFF FOR A FLUID ADMINISTRATION SYSTEM

(75) Inventors: Angela M. Noecker, St. Louis, MO (US); Glenn G. Fournie, Smithton, IL (US); John P. Moran, Herculaneum, MO (US)

(73) Assignee: Sherwood Services, AG (CH)

( * ) Notice: Subject to any disclaimer, the term of this patent is extended or adjusted under 35 U.S.C. 154(b) by 0 days.

(21) Appl. No.: 09/516,637

(22) Filed: Mar. 1, 2000

(51) Int. Cl.[7] .............................................. A61M 37/00
(52) U.S. Cl. ........................... 604/131; 604/250; 251/7; 251/4; 251/349
(58) Field of Search ........................... 604/9, 104, 156, 604/185, 131, 164.04, 167.04, 167.01, 250; 251/340, 349, 354, 117, 358, 28, 348, 14, 7, 4

(56) References Cited

U.S. PATENT DOCUMENTS

| | | | |
|---|---|---|---|
| 3,311,268 A | 3/1967 | Fields | 222/159 |
| 3,460,529 A | 8/1969 | Leucci | 128/2 |
| 3,547,401 A | 12/1970 | Beall et al. | 251/144 |
| 4,205,819 A * | 6/1980 | Soika | 251/340 |
| 4,263,932 A | 4/1981 | Laar et al. | 137/101.27 |
| 4,292,969 A * | 10/1981 | Raible | 251/340 |
| 4,395,260 A | 7/1983 | Todd et al. | 604/122 |
| 4,527,588 A * | 7/1985 | Tseo | 251/349 |
| 4,615,693 A | 10/1986 | Paradis et al. | 64/122 |
| 4,850,393 A | 7/1989 | Lashomb | 137/528 |
| 5,019,055 A | 5/1991 | O'Boyle | 604/249 |
| 5,261,459 A * | 11/1993 | Atkinson | 137/847 |
| 5,267,586 A | 12/1993 | Jankavaara | 137/565 |
| 5,396,925 A * | 3/1995 | Poli | 251/342 |
| 5,853,397 A * | 12/1998 | Shemesh | 604/247 |
| 5,868,715 A | 2/1999 | Tung | 604/256 |
| 5,954,485 A | 9/1999 | Johnson et al. | |

FOREIGN PATENT DOCUMENTS

| | | |
|---|---|---|
| CA | 2076512 | 8/1992 |
| DE | 4126088 | 1/1993 |

* cited by examiner

*Primary Examiner*—Ira S. Lazarus
*Assistant Examiner*—Tu Cam Nguyen
(74) *Attorney, Agent, or Firm*—Greensfelder, Hemker & Gale, P. C.

(57) ABSTRACT

The present invention relates an anti-free flow valve for a fluid administration systems having a tube assembly with a lumen formed through therethrough coupled to a pump. The anti-free flow valve comprises a body including a cylindrical portion having an opening and a tapered portion which has opposing beveled surfaces with ends that form a slit bounded by side walls. The opening communicates with the slit through a passage formed through the body which is adapted to receive the tube assembly therethrough. Fluid free flow through the tube assembly is prevented by the slit being placed in the closed position when the ends of the opposing beveled surfaces are urged together when the tube assembly is in a relaxed condition. However, when a tensile force is applied along the tube assembly the inner diameter of the lumen decreases which urges the ends of the opposing beveled surfaces away from one another and places the slit in the open position, thereby permitting fluid flow through the body.

23 Claims, 4 Drawing Sheets

VALVE CUFF FOR A FLUID ADMINISTRATION SYSTEM

BACKGROUND OF THE INVENTION

1. Field of the Invention

The present invention relates to a device for a fluid administration system, and more particularly to a valve for preventing fluid free flow in a fluid administration system. More specifically, the present invention relates to an anti-free flow valve having a cuff-like body fitted around a tube assembly.

2. Prior Art

Administering fluid containing medicine or nutrition to a patient is generally well-known in the art. Typically, fluid is supplied to a patient by a tube assembly which provides a fluid pathway between a fluid source and a patient. The fluid is supplied to the patient through the tube assembly by either an enteral connection which accesses a visceral organ (gastrointestinal feeding) of a patient or through a parenteral connection which accesses a non-visceral organ (intravenous feeding).

Fluid flow rate through the tube assembly may be manually controlled by a mechanical clip which is designed to progressively occlude the tube assembly and selectively impede fluid flow induced by the force of gravity. One such mechanical clip which operates to occlude a portion of the tube assembly is a conventional roller clamp that has a hollow body with opposed openings and a pair of angled slots formed opposite of one another transverse to the openings. The clip further includes a wheel having an axle which is coupled to the body through the slots. A portion of the tube assembly is then inserted through both the openings and the wheel axially advanced along the slots to pinch a portion of the tube against the body which progressively occludes the tube assembly. Although the mechanical clip operates to provide a cost-efficient method for controlling fluid flow rate, the clip must be manually actuated by the user. Further, the wheel of the mechanical clip can be inadvertently bumped or jostled out of position resulting in an inappropriate flow rate.

In order to better enhance fluid flow rate control in a fluid administration system, calibrated pumps have been utilized. One such calibrated pump is a peristaltic pump connected in-line along a portion of the tube assembly between the fluid source and the patient. The peristaltic pump advances the fluid through the tube assembly by progressively occluding successive portions of the tube assembly and urging each occluded portion forward. When a peristaltic pump is utilized to control the fluid flow rate, mechanical clips are typically not employed or are disengaged to prevent the clip from interfering with the operation of the pump.

Although peristaltic pumps have substantially advanced the art, further improvements are required. For example, once the tube assembly is disengaged from the pump fluid flow rate through the tube assembly becomes unrestrained as fluid is drawn through the tube assembly due to the force of gravity. This situation is known as fluid free flow and may present an undesirable, or even life-threatening situation, if left undetected because of the risk of overfeeding or over-medicating a patient.

In order to overcome the above-noted drawbacks to fluid administration systems utilizing pumps, several devices have been suggested which operate to automatically occlude a portion of the tube assembly and prevent fluid free flow when the tube assembly becomes disengaged from the pump while also permitting uninhibited fluid flow when the tube assembly is properly engaged to the pump. For instance, a variety of automatic occluders have been suggested to improve the art such as those disclosed in U.S. Pat. No. 4,689,043 to Bisha entitled "IV Tube Activator" which describes a clamp for use with a peristaltic pump. The clamp includes a V-shaped channel which is spring biased into a closed position where the narrow portion of the V-shaped channel is sized to substantially crimp, or occlude, a portion of the tube assembly and prevent fluid free flow therethrough. The clamp is placed in an open position by a handle which overlays the pump and depresses the springs such that the tube assembly is positioned within the wider portion of the V-shaped channel to permit unrestricted flow through the tube assembly when the pump is operating. When the handle is released, the V-shaped portion will automatically slide into the closed position and prevent fluid free flow by occluding a portion of the tube assembly.

Another automatic occluder is disclosed in U.S. Pat. No. 5,704,582 to Winterer, et al. entitled "Pinched Clipped Occluder for Infusion Sets" which describes a clip that is positioned between a housing and a cover of a pump. The clip has a plunger biased by a spring towards a portion of the tube assembly so that the lumen of the tube assembly becomes occluded by the plunger. Fluid flow through the tube assembly may only be established when the plunger is biased away from the lumen of the tube assembly which occurs when the cover is properly coupled with the housing. However, once the cover becomes disengaged from the housing, the plunger is automatically biased into the closed position by the spring to prevent fluid free flow.

Although both of the aforementioned automatic occluders have advanced the art, both devices are mechanically complex and prone to mechanical failure. In addition, the mechanical complexity of these devices also results in occluders which are expensive to manufacture. Accordingly, there is a need in the art for a simple valve device that is capable of preventing fluid free flow when the tube assembly is disengaged from the pump, while also being mechanically uncomplicated, reliable and low cost to manufacture.

OBJECTS AND SUMMARY OF THE INVENTION

In brief summary, the present invention overcomes and substantially alleviates the deficiencies present in the art by providing a cuff valve which is adapted to prevent fluid free flow in a fluid administration system having a pump and a tube assembly. The cuff valve of the present invention has a body fitted around the tube assembly for preventing fluid free flow when the tube assembly is disengaged from the pump while permitting uninhibited fluid flow when the tube assembly is engaged with the pump.

Preferably, the pump of the fluid administration system used with the present invention includes a rotor for advancing fluid through the tube assembly and first and second recesses formed adjacent the rotor for retaining portions of the tube assembly to the housing of the pump during operation of the system. The tube assembly includes three interconnected tube segments each having respective distal and proximal ends for providing a fluid pathway between a fluid source and a patient. The fluid source is connected to the distal end of the first tube segment, while the proximal end thereof is connected to the distal end of the second tube segment by a drip chamber having an abutment surface. The proximal end of the second tube segment is connected to the distal end of the third tube segment by a coupling having an external flange. Finally, the proximal end of the third tube segment is attached to a patient through either an enteral or parenteral connection.

The tube assembly is engaged with the pump by threading the second tube segment around the rotor with the abutment surface and external flange engaged within the first and second recesses, respectively, of the pump. Preferably, the length of the second tube segment as it is engaged around the rotor permits the abutment surface and the external flange to be properly captured by the first and second recesses and place the second tube segment in a stretched condition. Each of the tube segments has a lumen formed therethrough to allow the passage of fluid through the tube assembly.

Preferably, the cuff valve is fitted around the second tube segment adjacent the coupling by inserting the tube assembly through the cuff valve. The cuff valve of the present invention comprises a body having a cylindrical portion formed adjacent a tapered portion. The cylindrical portion of the cuff valve includes an opening and both the cylindrical portion and opening are generally circular in configuration. The tapered portion includes opposite beveled surfaces bounded by a pair of side walls. Preferably, the beveled surfaces are planar in shape, while the side walls have a generally rounded configuration. The tapered portion also includes a slit formed between the ends of the beveled surfaces. Finally, the opening communicates with the slit along a passage formed through the body to provide an unobstructed fluid pathway between the slit and the opening. When the slit is in an open position by urging the ends of the beveled surfaces away from one another, fluid may pass through the lumen of the tube assembly; however, when the slit is placed in the closed position the ends of the beveled surfaces come together and occlude the lumen of the tube assembly to prevent fluid free flow.

The cuff valve is engaged around the second tube segment such that the second tube segment extends through the opening and out the slit of the body. When the second tube segment is in a relaxed condition or disengaged from the pump, the slit is placed in the closed position by the ends of the beveled surfaces confronting one another and occluding the lumen of the second tube segment. However, once a tensile force is applied along the second tube segment by stretching it, the second tube assumes a stretched condition which urges the ends of the beveled surfaces away from one another as the inner diameter of the lumen is decreased. This action places the slit in the open position, thereby allowing fluid to pass through the lumen of the second tube segment. Once the applied tensile force along the second tube segment is released by disengaging the tube assembly from the rotor, the tube assembly automatically returns to the relaxed condition as the inner diameter of the lumen increases. The expansion of the lumen when the tube assembly is in the relaxed condition permits the ends of the beveled surfaces to come together and return the slit to the closed position. Alternatively, the slit may be placed in the open position by manually pinching the body of the cuff valve transverse to the slit which also causes the ends of the beveled surfaces to be urged away from one another.

In operation, the cuff valve of the present invention prevents fluid free flow whenever the tube assembly is disengaged from the pump while also permitting uninhibited fluid flow when the tube assembly is engaged around the rotor of the pump, or the cuff valve is manually actuated by the user. A portion of the tube assembly is inserted through the body of the cuff valve during manufacturing of the tube assembly or by the user. To utilize the cuff valve, the user first connects the tube assembly with the fluid source attached at one end and allows fluid to flow to the point where the cuff valve is attached to the tube assembly. The user then primes the tube assembly in order to evacuate air from remaining portions of the tube assembly and initiate fluid flow therethrough. Preferably, the tube assembly may be manually primed by stretching a portion of the tube assembly surrounding the cuff valve which urges the ends of the beveled surfaces away from one another and opens the slit to fluid flow through the lumen of the tube assembly. Air is then forced out through the remaining portions of the tube assembly. Alternatively, the user can manually prime the tube assembly by pinching the body of the cuff valve in a direction that is transverse to the slit. By pinching the cuff valve in this manner, the ends of the beveled surfaces are urged away from one another which opens the slit such that fluid flow may be established through the lumen of the tube assembly. Once all the air is cleared from the tube assembly, the proximal end of the third segment may be connected to the patient.

To regulate and urge the fluid through tube assembly, the tube assembly is connected to the pump. Specifically, the abutment surface of the drip chamber is engaged within the first recess of the pump and the second tube segment is stretched around the rotor. The external flange is then inserted into the second recess in order to retain the second tube segment in a stretched condition about the rotor. Due to the tensile force applied to the second tube segment, the second tube segment becomes taut and biases the ends of the beveled surfaces away from one another to the open the slit of the cuff valve. Once the slit is placed in the open position, fluid flow is established through the lumen of the second tube segment. Alternatively, the pressure of the fluid being pumped through the second tube segment and through the cuff valve by the pump may urge the ends of the beveled surfaces away from one another to permit fluid flow through the slit, or the combination of stretching the second tube segment and sufficient fluid flow pressure through the lumen of the tube assembly may also accomplish the same result. However, if the tube assembly becomes disengaged from the pump, either intentionally or unintentionally, the tensile force applied to the second tube segment is released and the tube assembly returns to its relaxed condition. In the relaxed condition, the ends of the beveled surfaces meet and place the slit in the closed position which occludes the lumen of the tube assembly and prevents fluid flow therethrough.

Accordingly, the primary object of the present invention is to provide a valve device which prevents fluid free flow.

A further object of the present invention is to provide a valve device that prevents fluid free flow when the tube assembly is disengaged from the pump, while permitting uninhibited fluid flow when the tube assembly is engaged to the pump.

Another object of the present invention is to provide a valve device which prevents fluid free flow while being mechanically simple and reduces the opportunity for mechanical failure.

Yet another object of the present invention is to provide a valve device that may be automatically or manually actuated.

Another further object of the present invention is to provide a valve device that is fitted around the tube assembly.

Still another object of the present invention is to provide a valve device which reduces manufacturing costs.

These and other objects of the present invention are realized in the preferred embodiment, described by way of example and not by way of limitation, which provides for a valve device for use in a fluid administration system to prevent fluid free flow.

Additional objects, advantages and novel features of the invention will be set forth in the description which follows, and will become apparent to those skilled in the art upon examination of the following more detailed description and drawings in which like elements of the invention are similarly numbered throughout.

BRIEF DESCRIPTION OF THE DRAWINGS

FIG. I is a partial fragmentary perspective view of a fluid administration system having a pump and a tube assembly coupled thereto with a cuff valve fitted around the tube assembly according to the present invention.

DETAILED DESCRIPTION OF THE INVENTION

Figure 1:
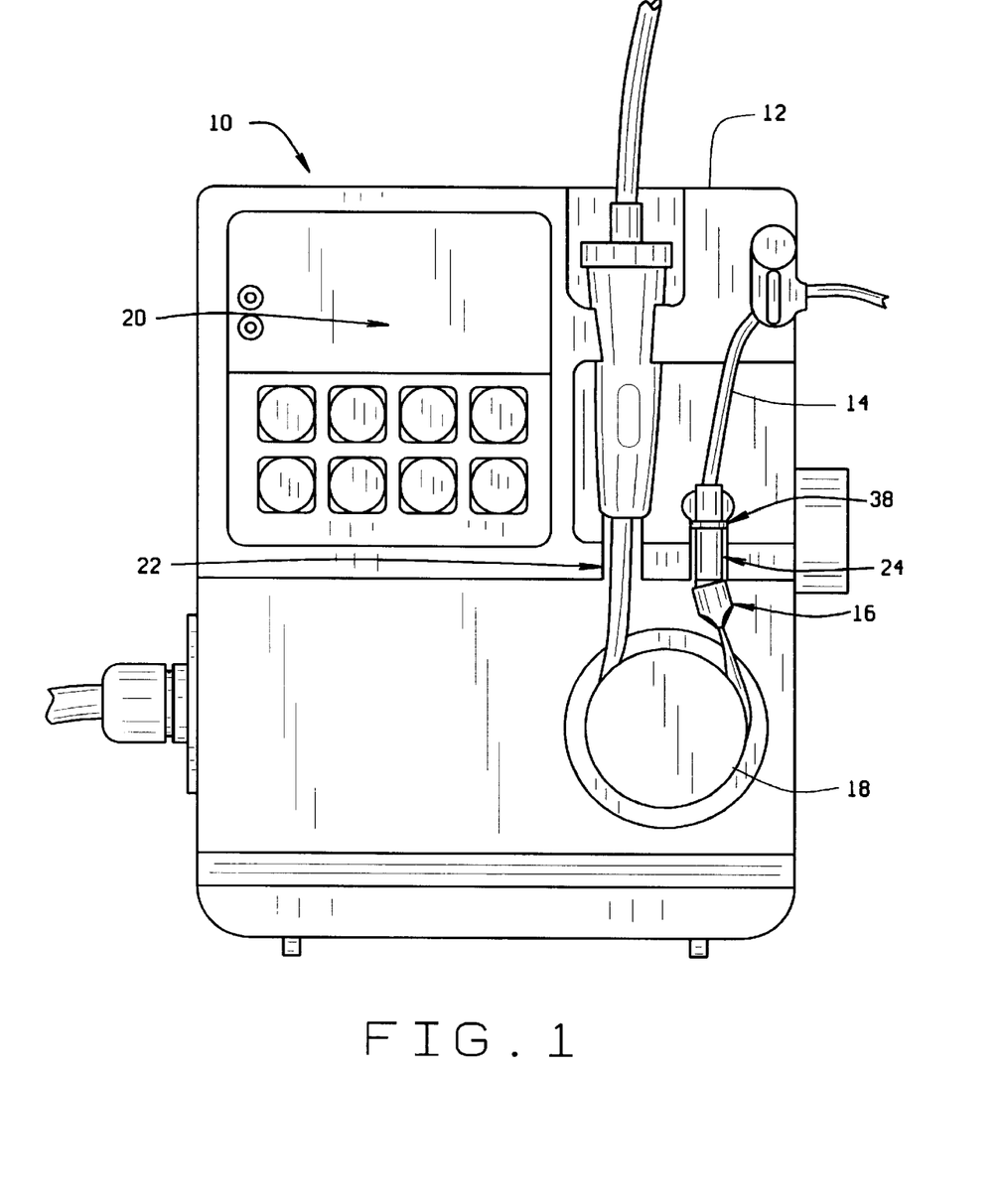

Referring to the drawings, the preferred embodiment of the cuff valve of the present invention is illustrated and generally indicated as 16 in FIG. 1. The cuff valve 16 is used in a fluid administration system 10 which comprises a tube assembly 14 engaged with a pump 12 at one end and a fluid source 40 connected at the other end of assembly 14. For ease of reference, proximal shall refer to the end of the valve device 16 or tube assembly 14 closest to fluid source 40, while distal shall refer to the end of device 16 or assembly 14 farthest from fluid source 40.

Pump 12 of the present invention is preferably a rotary peristaltic pump as illustrated in FIG. 1. Of course one skilled in the art can best appreciate that a variety of other pumps, such as a linear peristaltic pump, may be utilized without departing from the novel aspects of the present invention. Specifically, pump 12 includes a rotor 18 and a control panel 20 located adjacent rotor 18 which permits a user to monitor and adjust the rotation rate of rotor 18 for controlling fluid flow rate by pump 12. A first recess 22 and a second recess 24 are formed above rotor 18 for engaging portions of tube assembly 14 as will be discussed in greater detail below.

Figure 2:
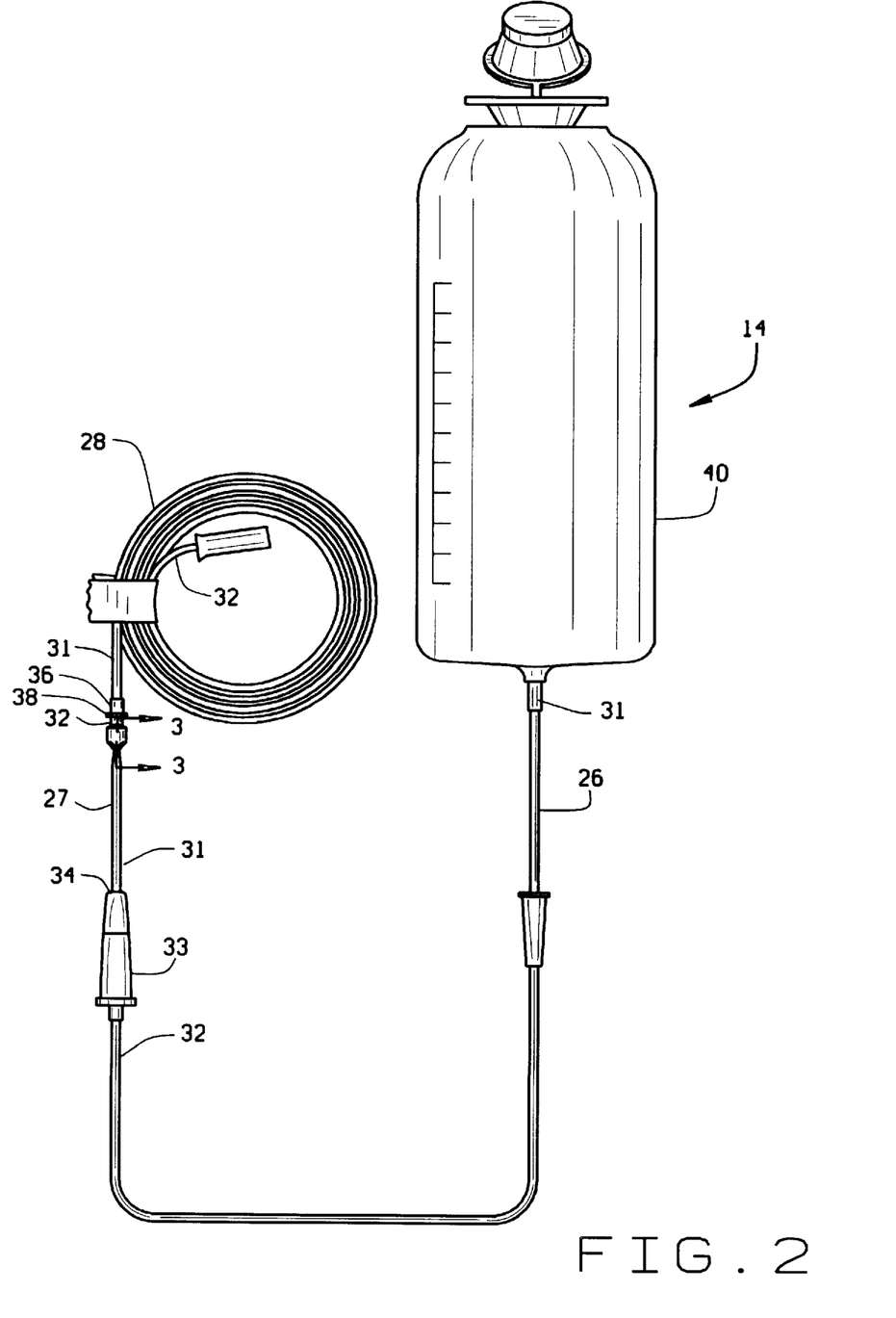
FIG. 2 is a front plan view of the tube assembly according to the present invention.

With reference to FIG. 2, tube assembly 14 includes a first tube segment 26, a second tube segment 27 and a third tube segment 28 which are in communication with one another. Each of the first, second and third tube segments 26, 27, and 28 have respective distal and proximal ends 31, 32. Connected to distal end 31 of first tube segment 26 is fluid source 40 for providing fluid to a patient while proximal end 32 thereof is attached to a drip chamber 33. As further shown, drip chamber 33 has an abutment surface 34 which interconnects proximal end 32 of first tube segment 26 with distal end 31 of second tube segment 27. Proximal end 32 of second tube segment 27 is then interconnected to distal end 31 of third tube segment 28 by a coupling 36 having an external flange 38. Finally, third tube segment 28 terminates at a proximal end 32 which is attached to an enteral or parenteral connection (not shown) made with the patient for delivery of fluid.

Figure 3:
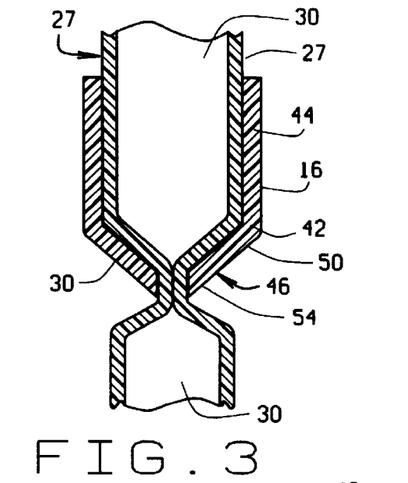
FIG. 3 is a fragmentary cross-sectional view taken along line 3—3 of FIG. 2 according to the present invention.

As illustrated in FIG. 1, abutment surface 34 and external flange 38 are sized and shaped to be captured within first recess 22 and second recess 24, respectively. Preferably, the length of second tube segment 27 permits abutment surface 34 and external flange 38 to be properly captured within the first recess 22 and second recess 24, respectively, while also stretching second tube segment 27 as it is engaged around rotor 18. Accordingly, the amount of tensile force applied along second tube segment 27 as it is engaged around rotor 18 may be varied by altering the length of tube segment 27. With reference to FIG. 3, each of the tube segments 26,27 and 28 includes a lumen 30 formed therethrough by which fluid may pass from fluid source 40.

Figure 4:
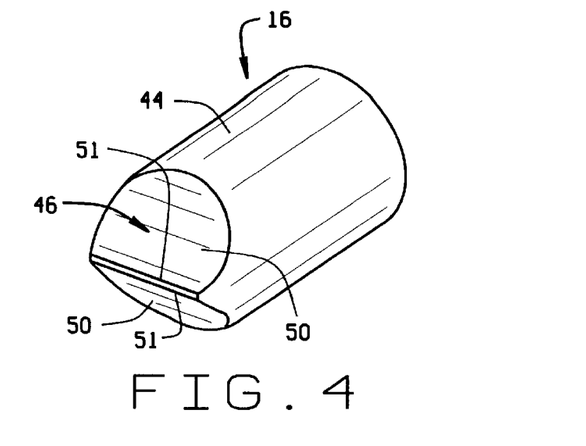
FIG. 4 is a perspective view of the cuff valve according to the present invention.
Figure 5:
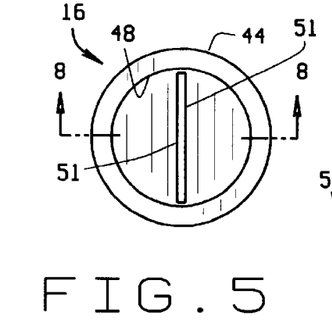
FIG. 5 is a rear view of the cuff valve according to the present invention.
Figure 6:
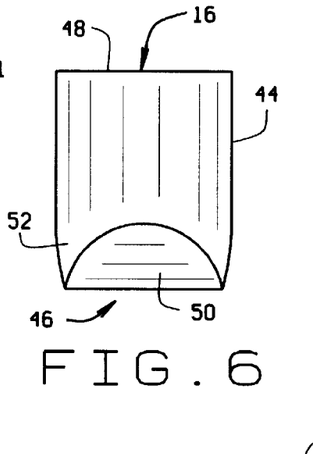
FIG. 6 is a side view of the cuff valve according to the present invention.
Figure 7:
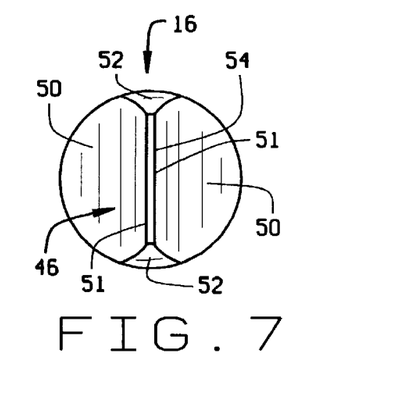
FIG. 7 is a front view of the cuff valve according to the present invention.
Figure 8:
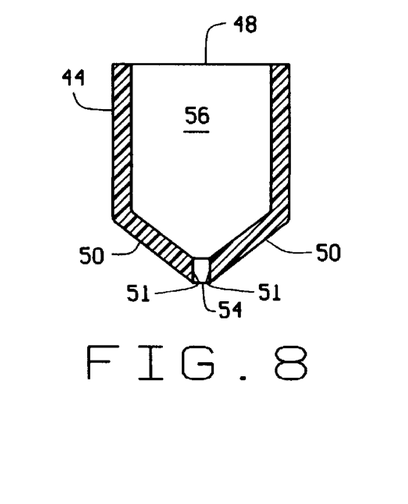
FIG. 8 is a cross-sectional view of the cuff valve taken along line 8—8 of FIG. 5 according to the present invention.

Referring to FIGS. 3 and 4, cuff valve 16 comprises a flexible body 42 having a cylindrical portion 44 formed adjacent a tapered portion 46. As shown in FIG. 5, cylindrical portion 44 further includes an opening 48 which is generally circular in crosssection. With reference to FIG. 6, the tapered portion 46 includes opposite beveled surfaces 50 bounded by a pair of side walls 52. Preferably, the beveled surfaces 50 are planar in shape, while side walls 52 have a generally rounded configuration. As shown in FIG. 7, the tapered portion 46 further includes a slit 54 formed between ends 51 of the beveled surfaces 50. As seen in FIG. 8, opening 48 communicates with slit 54 along a passage 56 formed through body 42 to provide a pathway between slit 54 and opening 48.

Figure 10:
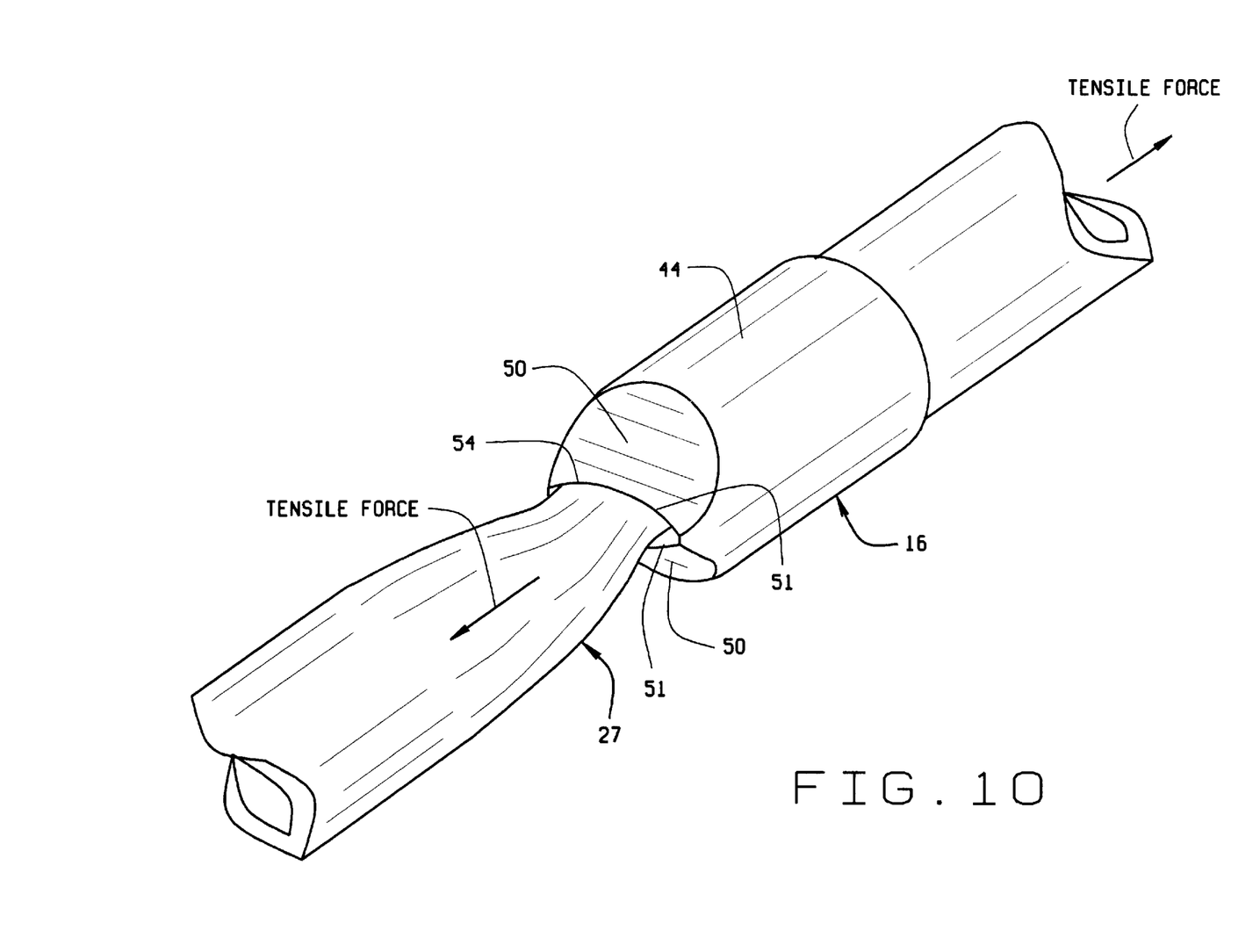
FIG. 10 is a perspective view of the cuff valve in the open position according to the present invention.

Cuff valve 16 is fitted around second tube segment 27 during manufacturing such that tube segment 27 extends through opening 48 and out slit 54. Preferably, cuff valve 16 is positioned along second tube segment 27 adjacent coupling 36, although valve 16 may be positioned along any portion of tube assembly 14 without departing from the scope of the present invention. When tube assembly 14 is in the relaxed condition, slit 54 is placed in a closed position which occludes second tube segment 27 and prevents fluid flow therethrough. As shown in FIG. 10, when a tensile force is applied along second tube segment 27, tube segment 27 is placed in the stretched condition, thereby urging the ends 51 of the beveled surfaces 50 away from one another as the inner diameter of the lumen 30 is decreased and body 42 becomes elongated. This action places slit 54 in the open position and permits fluid flow through lumen 30. As noted above, sufficient fluid pressure through lumen 30 and/or tensile force applied along second tube segment 27 may also place slit 54 in the open position for passage of fluid. However, when the tensile force applied along second tube segment 27 is released and tube assembly 14 returns to a relaxed condition, slit 54 is placed in a closed position, as shown in FIG. 3, and the ends 51 of the beveled surfaces 50 are brought together and occlude tube segment 27 to prevent fluid free flow through slit 54.

Cuff valve 16 is preferably formed from an elastically deformable material, for example silicone rubber, although any suitable elastically deformable material may be utilized without departing from the teachings of the present invention. The amount of tensile force that is applied along second tube segment 27 sufficient to place slit 54 in the open position may be changed by modifying the length of tube segment 27. A second tube segment 27 with a greater length would apply a lesser tensile force therealong than a tube segment with a shorter length when engaged around the rotor 18.

Figure 9:
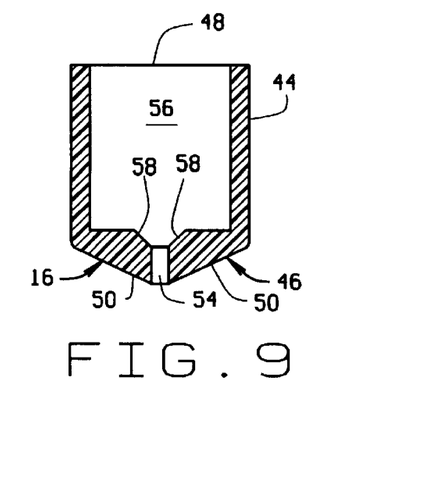
FIG. 9 is a cross-sectional view of an alternative embodiment of the cuff valve taken along line 8—8 of FIG. 5 according to the present invention.

In an alternative embodiment, cuff valve 16 may be formed having a tapered portion 46 which is generally dome shaped. As shown in FIG. 9, tapered portion 46 includes a slit 54 with angled interior surfaces 58 formed adjacent slit 54 which are inwardly angled towards slit 54. The angled surfaces 58 facilitate insertion of the second tube segment 27 through slit 54.

In operation, the user of the present invention connects tube assembly 14 having a cuff valve 16 attached thereto to a fluid source 40 and permits fluid to flow through lumen 30 until the fluid reaches the point where cuff valve 16 is attached. With tube assembly 14 in a relaxed condition and disengaged from pump 12, cuff valve 16 prevents fluid free flow into third tube segment 28. Preferably, air is cleared from third tube segment 28 when the user primes tube assembly 14 by applying a tensile force along the area of the tube assembly 14 adjacent cuff valve 16 in order to place tube assembly 14 in the stretched condition and open slit 54 to fluid flow. Applying a tensile force causes second tube segment 27 to stretch which in turn exerts a force to body 42 transverse to slit 54 as the decrease in the inner diameter of lumen 30 urges the ends 51 of the beveled surfaces 50 away from one another. As the inner diameter of lumen 30 decreases, body 42 elongates and slit 54 is placed in the open position. Alternatively, tube assembly 14 may be primed by directly pinching cuff valve 16 in a direction that is transverse to slit 54. By pinching cuff valve 16 in this manner, the ends 51 of the beveled surfaces 50 are urged away from one another and slit 54 is placed in the open position which allows fluid flow through lumen 30. Once the tube assembly 14 has been primed, the proximal end 32 of the third tube segment 28 may be connected to the enteral or parental connection on the patient.

To regulate and urge fluid flow through tube assembly 14, tube assembly 14 is engaged to pump 12 as illustrated in FIG. 1. Specifically, abutment surface 34 of drip chamber 33 is positioned within first recess 22 and second tube segment 27 is engaged around a portion of rotor 18. External flange 38 is then inserted into second recess 24 such that a tensile force is applied along second tube segment 27 and tube segment 27 is maintained in a stretched condition. As the tensile force is applied along second tube segment 27, tube segment 27 becomes stretched and taut which biases the ends 51 of the beveled surfaces 50 away from one another and places slit 54 in the open position. Once slit 54 is placed in the open position as shown in FIG. 10, fluid flow may be established through lumen 30. Moreover, pressure forced by fluid passing through lumen 30 by pump 12, alone or in combination with the applied tensile force, may also open lumen 30 to fluid flow. However, if tube assembly 14 becomes disengaged from pump 12 the tensile force applied along second tube segment 27 is released and tube assembly 14 returns to its relaxed condition. In the relaxed condition, the ends 51 of the beveled surfaces 50 close together, thereby placing slit 54 in the closed position and preventing fluid free flow therethrough.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

What is claimed is:

1. A cuff valve for use with a fluid administration system connected between a patient and a fluid source by a tube assembly having a lumen formed therethrough, the valve cuff comprising:

a body attached to the tube assembly, said body including a cylindrical portion having an opening formed therethrough and a tapered portion formed adjacent said cylindrical portion, said tapered portion having beveled surfaces formed opposite of one another with ends defining a slit therebetween, said slit being in communication with said opening and in contact with said tube assembly, wherein when said slit is placed in a closed position, fluid flow through the lumen is prevented and when said slit is placed in an open position fluid flow is permitted through the lumen.

2. The cuff valve according to claim 1, wherein fluid flow through the tube assembly is prevented by occlusion of the lumen by said slit.

3. The cuff valve according to claim 1, wherein said opening communicates with said slit through a passage from through said body.

4. The cuff valve according to claim 1, wherein the tapered portion further comprises a pair of side walls opposite of one another and approximately transverse to said beveled surfaces.

5. The cuff valve according to claim 1, whereon said slit is placed in said open position when a tensile force is applied along the tube assembly.

6. The cuff valve according to claim 1, whereon said body is attached to the tube assembly by insertion of the tube assembly through said opening and out said slit of said body.

7. A tube assembly for use with a fluid administration system connected between a patient and a fluid source by a tube assembly, said tube assembly comprising:

at least one tube segment having a lumen therethrough; and a valve device fitted over a portion of said at least one tube segment, said valve device comprising a cylindrical portion having an opening and a tapered portion formed adjacent said cylindrical portion, said tapered portion including a pair of beveled surfaces having ends opposite one another with said ends defining a slit therebetween, wherein when a tensile force is applied along said at least one tube segment said slit is placed in an open position, and when said tensile force is released, said slit is placed in the closed position.

8. The tube assembly according to claim 7, wherein when said slit is in the open position fluid flow is permitted through said lumen and when said slit is in the closed position fluid flow is prevented through said lumen.

9. The tube assembly according to claim 7, wherein said valve device further comprises a passage interconnecting said opening and said slit.

10. The tube assembly according to claim 5, wherein said tapered portion further comprises a pair of side walls opposite one another and approximately transverse to said beveled surfaces.

11. A fluid administration system connected between a patient and a fluid source by a tube assembly, said tube assembly comprising:

a pump;

at least one tube segment having a lumen forced therethrough, said at least one tube segment being attached to said pump; and a hollow valve device, a portion of said at least one tube segment being inserted through said hollow valve device, said valve device including a cylindrical portion having an opening and a tapered portion formed adjacent said cylindrical portion, said tapered portion including beveled surfaces with ends formed opposite of one another and defining a slit therebetween, said slit being in communication with said opening, wherein in a closed position said slit closes fluid flow through said lumen and in an open position said slit permits fluid flow through said lumen.

12. The fluid administration set according to claim 11, wherein when said at least one tube segment is attached to said pump, a tensile force is applied along said at least one tube segment, thereby placing said slit in said open position.

13. The fluid administration set according to claim 11, wherein said valve device further comprises a passage interconnecting said opening and said slit.

14. The fluid administration set according to claim 11, wherein the tapered portion of said valve device further comprises a pair of side walls opposite of one another and approximately transverse to said beveled surfaces.

15. The fluid administration system according to claim 11, wherein said pump further comprises:

a rotor;

a first recess formed adjacent said rotor; and a second recess formed adjacent said rotor.

16. The fluid administration system according to claim 15, wherein said at least one tube segment comprises:

a first tube segment;

a second tube segment connected to said first tube segment; and a third tube segment connected to said second tube segment.

17. The fluid administration system according to claim 16, wherein said tube assembly further comprises:

a drip chamber having an abutment surface interconnected between said first tube segment and said second tube segment; and a coupling having an external flange interconnected between said second tube segment and said third tube segment.

18. The fluid administration system according to claim 17, wherein said abutment surface is engaged with said first recess and wherein said external flange is engaged within said second recess.

19. A method for preventing fluid free flow during priming of a fluid administration system comprising a pump and a tube assembly, the fluid administration system further including a pump, the tube assembly having a lumen therethrough, said method comprising the steps of:

(a) providing a fluid administration system further including a valve device fitted over the tube assembly, the valve device comprising a cylindrical portion having an opening and a tapered portion formed adjacent said cylindrical portion, said tapered portion further having a pair of beveled surfaces with ends formed opposite of one another and defining a slit therebetween in communication with said opening and in contact with said the tube assembly;

(b) connecting one end of the tube assembly to the fluid source;

(c) establishing fluid flow from the fluid source through the tube assembly to the point where the valve device is located;

(d) actuating the valve device;

(e) establishing fluid flow throughout the remaining portions of the tube assembly; and (f) attaching the other end of the tube assembly to the patient.

20. The method according to claim 19, wherein said step of actuating the valve device comprises:

applying a force to the valve device in a direction approximately transverse to the slit in order to open the ends of the pair of beveled surfaces away from one another and open said slit to fluid flow through the lumen.

21. The method according to claim 19, wherein said step of actuating the valve device comprises:

stretching tube assembly adjacent the valve device such that the tube assembly becomes taut and urges the ends of the beveled surfaces sway from one another to open said slit and allow fluid flow through the lumen.

22. The method according to claim 19, wherein said step (d) causes remaining air to be evacuated from the tube assembly.

23. The method according to claim 19, wherein said step (b) places the slit is in the closed position and prevents fluid flow through the valve device.

* * * * *

UNITED STATES PATENT AND TRADEMARK OFFICE
CERTIFICATE OF CORRECTION

PATENT NO. : 6,454,742 B1
DATED : September 24, 2002
INVENTOR(S) : Angela M. Noecker et al.

It is certified that error appears in the above-identified patent and that said Letters Patent is hereby corrected as shown below:

Column 4,
Lien 29, delete "to the open the slit" and insert -- to the open slit --.

Column 8,
Line 26, delete "a passage from" and insert -- a passage --.

Column 10,
Line 39, delete "surfaces sway" and insert -- surfaces away --.
Line 45, delete "the slit is in" and insert -- the slit in --.

Signed and Sealed this

Twenty-fourth Day of August, 2004

JON W. DUDAS
*Director of the United States Patent and Trademark Office*